US006676980B2

(12) United States Patent
Quintanilla Almagro et al.

(10) Patent No.: US 6,676,980 B2
(45) Date of Patent: Jan. 13, 2004

(54) METHOD FOR PREPARING AN OLEA EUROPAEA EXTRACT AND METHOD OF USE OF THE SAME

(75) Inventors: Eliseo Quintanilla Almagro, Alicante (ES); Ginés Aviles Olmos, Alicante (ES); José Antonio Tovar Oliva, Alicante (ES); Joaquin Diaz Alperi, Alicante (ES); José Sempere Ortells, Alicante (ES); José Pardo Zapata, Alicante (ES)

(73) Assignee: Asac Compañia de Biotecnologia e Investigacion S.A., Alicante (ES)

( * ) Notice: Subject to any disclaimer, the term of this patent is extended or adjusted under 35 U.S.C. 154(b) by 0 days.

(21) Appl. No.: 09/913,029
(22) PCT Filed: Dec. 21, 2000
(86) PCT No.: PCT/ES00/00482
§ 371 (c)(1), (2), (4) Date: Mar. 8, 2002
(87) PCT Pub. No.: WO01/47537
PCT Pub. Date: Jul. 5, 2001

(65) Prior Publication Data
US 2003/0017217 A1 Jan. 23, 2003

(30) Foreign Application Priority Data
Dec. 23, 1999 (ES) .............................. 0000064
(51) Int. Cl.[7] .............................................. A61K 35/78
(52) U.S. Cl. ................. 424/769; 424/774; 514/885
(58) Field of Search ................. 424/769, 774; 514/885

(56) References Cited

U.S. PATENT DOCUMENTS 4,117,603 A * 10/1978 Smith

FOREIGN PATENT DOCUMENTS

| FR | 2507477 | 12/1982 |
| WO | WO 9614064 | 5/1996 |
| WO | WO 9938383 | 8/1999 |

OTHER PUBLICATIONS

J Chem. Soc. (1908), vol. 93–94, pp891–904. Power et al. The Constituents of Olive Leaves.*
Proc. Chem. Soc. (1908), vol. 24, p. 117. Power et al. The constituents of olive leaves.*
De Pablo et al, *J. Clin. Biochem. Nutr.*, 25(*1*):11–23 (1998).
Yaqoob et al, *Immunology Letters*, 41(*2–3*):241–247 (1994).
Sanderson et al, *J. Nutr. Environ. Med.*, 5(2):119–132 (1995).

* cited by examiner

*Primary Examiner*—Christopher R. Tate
*Assistant Examiner*—Michele Flood
(74) *Attorney, Agent, or Firm*—Sughrue Mion, PLLC

(57) ABSTRACT

Procedure for obtaining *Olea Europea* extracts from *Olea Europea* leaves dried at less than 35° C. with alkanols at a low temperature and extract purification New pharmacological applications of *Olea Europea* extracts as an agent reinforcing cellular immunity and delayed hypersensitivity in healthy humans, activating and proliferating T-lymphocytes, Natural Killer cells, monocytes and granulocytes, and pro-inflammatory cytokins.

11 Claims, No Drawings

METHOD FOR PREPARING AN OLEA EUROPAEA EXTRACT AND METHOD OF USE OF THE SAME

This application is a §371 of PCT/ES00/00482, filed Dec. 21, 2000.

TECHNICAL SCOPE OF THE INVENTION

This invention describes a procedure for obtaining stabilised vegetable extracts from *Olea europaea* by extraction from the leaves dried at less than 35° C., purification of the extract and evaporation of the extract. The extract obtained contains a high Oleuropein content and a high raw material yield.

This invention describes new therapeutic applications of *Olea europaea* extracts as an immunological agent, activating and proliferating T-lymphocytes, Natural Killer (NK) cells, monocytes and granulocytes in healthy humans, and increasing pro-inflammatory cytokines.

STATE OF THE ART

Oleuropein is a bitter glycoside that is found in the fruit, roots, bark and especially the leaves of *Olea europaea*. It is the active component of *Olea europaea* extracts, together with the flavonoids present in the extracts.

Methods for preparing vegetable extracts from *Olea europaea* leaves with pharmacological activity have been described in U.S. Pat. No. 5,714,150 and WO9614064.

U.S. Pat. No. 5,714,150 describes a procedure for extraction from *Olea europaea* leaves by maceration, using as an extractant an alcohol/water mix in an approximate proportion of 75%–25% at a temperature between 20–88° C., obtaining an extract with a Oleuropein content of 35%.

Patent application WO9614064 describes obtaining *Olea europaea* extracts with pharmacological activity using as an extractant water and/or water/alcohol solutions at a wide range of temperatures between 20–100° C., using dried leaves.

However, there is no document in the State of the Art describing the purification of the extract or drying the leaves at a low temperature.

According to the documents in the State of the Art, vegetable extracts from *Olea europaea* and Oleuropein have shown pharmacological properties, especially as anti-viral drugs.

The first medicinal use of this extract date from the early 1800's, when it was used in liquid form to treat malaria. Since then it has had many medical applications. Among the most significant effects described for this compound is its anti-infectious activity in the presence of a virus, although it is also effective against bacteria, fungi and some intracellular parasites. This anti-infectious activity against these pathogens has been related to a direct effect of the elenolic acid; in the case of viruses, the product's capacity to penetrate into the infected cells and directly inactive viral replication has been described, among others, either interfering, for example, with virus-critical amino-acids or, in the case of retroviruses, neutralising the production of reverse transcryptase or proteases. The many mechanisms used by Oleuropein to inactivate bacteria include a direct lytic effect on their external walls.

No document included in the State of the Art has shown the effect of *Olea europaea* extracts on the immune system, reinforcing Cellular Immunity and delayed Hypersensitivity in humans by the activation and proliferation of T-lymphocytes, Natural Killer (NK) cells, monocytes and granulocytes in healthy humans.

The CD16 membrane antigen, also known as a type II IgG Fc fragment receptor, is usually express in NK cells, granulocytes and macrophages. Most of the antibody-dependent cellular toxicity, or ADCC, corresponds to NK cells and a small population of cytotoxic T-lymphocytes that also express the CD16 marker, the Fc receptor that mainly binds human IgG1 and IgG3 complexes. The ADCC provides these cytotoxic cells with a mechanism with which, making use of the specificity of the antigen-antibody bond, they are able to direct or focus their cytotoxic activities. The CD16 present in the granulocyte and macrophage membrane also helps these cells in the phagocytosis. So a drug that increases this marker's expression in different cell populations can generate an activation of NK cells and a small population of cytotoxic T-lymphocytes, increasing their function as cytotoxic cells. The function of NK cells in the immune system is to defend the body from viral infections, eliminating virus-infected cells. The increased expression of CD16 in granulocytes and macrophages can reinforce the main function of these cells in the inflammatory process, which is the elimination of bacteria, fungi and other pathogens by phagocytosis.

On the other hand, for the cells in the immune system to function effectively requires contact with other cells or the extracellular matrix, so that they recognise the situation. The surface of the leukocytes not only possesses specific receptors that allow them to interact and become active in response to certain stimulants, but they also express a large number of molecules that are identified as adhesion molecules. These leukocyte molecules will act as receptors of ligands in other cells (in this case acting as counter-receptors) or amino-acid sequences present in different extracellular matrix proteins such as collagen, fibronectin, laminin and others.

Adhesion molecules also collaborate in cellular activation, sending co-activating signals to the cell interior. Depending on their structure, they can be classified into three general categories:
1.—The selectins
2.—Those that belong to the family of the integrins.
3.—Those that belong to the super-family of the immunoglobulins.

The CD11a and CD11b function-associated antigens are the alpha-chains of the LFA-1 and Mac-1 integrins, respectively. Both of them belong to the family of the $\beta 2$ integrins. These membrane molecules are fundamental for the normal development of the inflammatory process, fundamentally mediating the final adhesion of the leukocytes to the vascular endothelium, the extravasation and the migration to the inflammatory foci. Their increased expression or new expression in the cellular membrane is usually a consequence of the release of pro-inflammatory cytokins such as IL-1, TNF-$\alpha$, IL-8 etc. In normal conditions, inflammation is a physiological phenomenon aimed at eliminating pathogen agents through phagocytosis and restoring the damaged tissue. The increased expression obtained by a drug in lymphocytes on the CD11a molecule and in lymphocytes and monocytes on the CD11b molecule, together with the increase in the plasmatic levels of pro-inflammatory cytokins such as IL-1$\beta$ and IL-8, implies an activation of lymphocytes, monocytes and granulocytes that will finally result in a reinforcement of the inflammatory response. IL-8, which belongs to the family of the chemokins, also has the capacity to stimulate the movement of leukocytes (chemokinesis) and directed movement (chemotaxis), especially of neutrophils.

Moreover, the increased expression of CD25 membrane markers in monocytes and of CD69 in lymphocytes and monocytes produced by a drug, implies an activation of these populations, reinforcing the immune system with the administration of the drug.

The procedures for extraction from *Olea europaea* described in the State of the Art provide extracts with a high Oleuropein content, but these documents do not describe the Oleuropein yield from the raw material, *Olea europaea* leaves. Drying *Olea europaea* leaves at a low temperature leads to a greater extraction yield and obtains an extract with a high Oleuropein content, without losing the active components and maintaining all the pharmacological properties of the extract. Drying *Olea europaea* leaves at a temperature of less than 35° C. provides a raw material with a Oleuropein content of 5% compared with the 0.3% described in the State of the Art.

The use of water, and then membrane filtration, to obtain Olea extracts has the advantage of a greater level of selectivity in the extraction, eliminating the least polar components of the extract such as chlorophylls, polyphenols, fats and alkylphenols, with no pharmacological activity.

The action of the Oleuropein and the flavonoids present in *Olea europaea* extracts on the immune system by activating T-lymphocytes, Natural Killer cells, monocytes and granulocytes, reinforces the virus and bacteria elimination activity. This action is independent from viral replication or the lysis of the bacterial wall. It also reinforced cell immunity against bacteria, viruses and other cellular growth parasites, together with delayed hypersensitivity, generating the release of pro-inflammatory cytokines.

OBJECT OF THE INVENTION

This invention describes a new procedure for obtaining *Olea europaea* extracts, containing Oleuropein and flavonoids, consisting of drying protected from light at less than 35° C., extraction by maceration with an alcohol with low molecular weight at a temperature of less than 20° C., evaporation of the solvent, treating the extract with water, membrane filtration and freeze-drying.

This invention describes the pharmacological activity of *Olea europaea* as an immunological agent, reinforcing antibody dependent cytotoxicity (ADCC), and in broader terms, cellular immunity and delayed hypersensitivity, by the activation and proliferation of T-lymphocytes, Natural Killer cells, monocytes and granucolytes in healthy humans.

DETAILED DESCRIPTION OF THE INVENTION

The water content in *Olea europaea* leaves is around 6%, measured by drying losses for 3 hours at 105° C. Dehydrating is at a temperature of less than 35° C., away from direct light, to avoid the decomposition of the active ingredients. It has been demonstrated that *Olea europaea* leaves are very sensitive to temperature and direct light, which change their content in active ingredients.

Oleuropein content variations with different temperatures are shown on table 1.

TABLE 1

Oleuropein content in different drying conditions

| Drying at 50° C. | Drying at 35° C. | Drying at ambient temperature |
| --- | --- | --- |
| 1.3% | 5.8% | 7.3% |
| 1.8% | 9.5% | 10.1% |
| 4.6% | 8.3% | 10.1% |
| 3.8% | 4.7% | 6.6% |
| 2.4% | 4.0% | 5.8% |
| 3.1% | 5.3% | 7.6% |
| 3.0% | 3.5% | 6.8% |
| 1.8% | 3.6% | 6.5% |

The drying conditions, then, are critical for the degradation kinetics of Oleuropein. Unsuitable drying conditions provoke the decomposition of the Oleuropein and, therefore, a yield loss.

The stability of the Oleuropein is also affected by sunlight. For an Oleuropein content of 3.5% in dry leaves after 12 hours of exposure to the sun at 20° C. the Oleuropein content falls to 0.82%. Therefore, drying the *Olea europaea* leaves at a temperature of less than 35° C. provides a raw material with a minimum content of 5% compared to the 0.3% described in the State of the Art.

The extraction of the leaves is carried out at a temperature of less than 20° C. by alkanols with a low molecular weight of a purity greater than 95%, and the alkanols that provide the best results are methanol and ethanol.

The leaves are extracted with an approximate proportion of leaf for each 6 liters of solvent by maceration for 18 hours at a temperature of less than 20° C. The liquid extracts are concentrated to syrup consistency, preferably by high vacuum, at a temperature of less than 40° C., until the content in solids is around 80%.

The syrup is treated with purified water and filtered through sterile plates, avoiding microbial contamination and eliminating the pharmacologically inactive components from the extract, including chlorophylls, polyphenols, alkylphenols, mucilages, etc.

The solvent is removed from the solution by dry-freezing at −40° C. with a vacuum and heat of less than 35° C., obtaining a dry extract in the form of a greenish powder.

The yield of the extracts is around 25% of the raw material and this extract contains 18% Oleuropein and 5% flavonoids. Liquid chromatography has identified hesperidin, rutin and luteolin-7-glucoside. The Olea extract can be purified by an expert, using known techniques such as chromatography, fractioned crystallisation, etc., obtaining extracts with a higher Oleuropein content.

The *Olea europaea* extract has shown pharmacological activity on the immune system of healthy humans after the administration of a pharmaceutical product that contained 300 mg of *Olea europaea* extract, with 18% Oleuropein and 5% flavonoids, together with pharmaceutically acceptable excipients. The doses received by the subjects studies were 300 mg of extract (1 tablet)/6 hours and 600 mg of extract (2 tablets)/6 hours. Therefore, six individuals took 1.2 grams of extract a day and another six took 2.4 grams of extract.

The following parameters were analysed by Cell Sorter Vantage and Direct double-marker Immunofluorescence (fluorescein-FITC or phycoerythrin-PE) in total blood with EDTA:

Cell line markers (leukocyte populations): CD3, CD4, CD8, CD16, CD19, CD56, CD11a, CD11b and CD14.

Cellular activation markers: CD69 and CD25.

Combinations of the previous monoclones.

Different points of analysis were selected, depending on the combinations of monoclonal antibodies, for lymphocytes, monocytes and polymorphonuclears. The monoclonal combinations were as follows:

CD3-FITC/CD25-PE
CD4-FITC/CD8-PE
CD19-FITC/CD25-PE
CD3-PE/CD16-FITC/CD56-FITC
CD16-FITC/CD56-FITC/CD25-PE
CD11a-FITC/CD25-PE
CD11b-FITC/CD25-PE
CD14-FITC/CD25-PE

All these parameters were analysed before taking the drug (D0), 24 hours after taking the drug (D1), 72 hours after taking the drug (D3) and on day 11 (D11). Therefore, a total of 4 extractions were taken (10 ml/extraction) from each patient. Besides the tube of blood with EDTA, two tubes were used for serum in each of the 4 extractions; one of them was used for an elementary biochemical analysis and the other was frozen at −20° C. for later use. This last tube was used to determine plasmatic levels of cytokins by ELISA. The cytokins measured were interleukin 1β (IL-1β), interleukin 2 (IL-2), interleukin 8 (IL-8) and interferon gamma (INF-γ).

The results of the study were as follows:

1.—No significant changes were observed in the elementary biochemical or haematological analysis before and after taking the product.
2.—There were no significant differences between the group that took 1.2 g/day and the group that took 2.4 g/day.
3.—There is a tendency to increase the percentage of cells with CD16 expression both in lymphocytes and in granulocytes.
4.—An increase is observed in the percentage of cells with CD11b expression, both in lymphocytes and in monocytes and an increase of CD11 a expression in monocytes, and no significant changes were observed in the kinetics of the expression of lymphocyte populations CD3+, CD4+, CD8+ and CD19+.
5.—An increase in the expression of CD14 in monocytes is observed.
6.—Important and significant increases are observed in the expression of the early (CD69) and late (CD25) activation, both in lymphocytes and in monocytes.
7.—Tendency to increase the plasmatic levels of certain pro-inflammatory cytokines such as IL-1β and IL-8, particularly on the third day of taking the product.

The previous results and the increase in the plasmatic levels of inflammatory cytokines show the reinforcement of cellular immunity and delayed hypersensitivity by the activate of T lymphocytes, NK cells, monocytes and granulocytes.

The invention is described by these examples, which do not limit the invention's scope.

EXAMPLE 1

Illustrating Extraction from *Olea europaea* Leaves

106 Kilograms of *Olea europaea* leaves with a water content of 6%, are dried in a forced air artificial dryer at a temperature lower than 35° C.

The dried leaves are crushed by a cryogenisation process.

The dried *Olea europaea* leaves, with an Oleuropein content of 6.23% are extracted with 600 liters of 95% methanol for 18 hours at 20° C. The process is repeated 3 more times until extraction is exhausted.

The filtered liquid extracts are concentrated in a vacuum at less than 40° C. to obtain 32 kilos of a syrupy substance. The syrup is suspended in water and purified by sterile filtration. The aqueous solution is concentrated by freeze-drying, obtaining 25 kilos of a dry *Olea europaea* extract, with a Oleuropein content of 21.9% and 5% of flavonoids (hesperidin, rutin, luteolin-7-glucoside). Yield of the extract: 25%.

EXAMPLE 2

Illustrating the Variation of the Immunological Parameters in Health Humans with an Intake of Olea Extract

| Parameter | T = 0 | 1 day | 3 days | 10 days |
|---|---|---|---|---|
| LymphocytesCD16+ (%) | 15 | 20 | 21 | 24 |
| LymphocytesCD11a+ (%) | 7 | 11 | 27 | 27 |
| MonocytesCD11b+ (%) | 72 | 71 | 83 | 92 |
| MonocytesC14+ (%) | 69 | 67 | 81 | 84 |
| CD69 (%) | 3 | 3 | 14 | 10 |
| CD25 (%) | 1 | 5 | 16 | 12 |
| IL-1β (pg/ml) | 6 | 32 | 30 | 4 |
| IL-8 (pg/ml) | 101 | 180 | 181 | 169 |

EXAMPLE 3

Illustrating the Pharmaceutical Formulation Used

| | |
|---|---|
| *Olea europaea* extract | 300 mg |
| Microcrystalline cellulose | 154 mg |
| Magnesium stearate | 3 mg |

What is claimed is:

1. A method for preparing an *Olea europaea* extract having an oleuropein content of greater than 18% and a flavonoid content of greater then 5%, comprising the steps of:
    (A) drying *Olea europaea* leaves at a temperature of lower than 35° C.;
    (B) contacting the resulting dried *Olea europaea* leaves with a solvent to obtain a solvent extract;
    (C) purifying the resulting solvent extract to obtain a purified solvent extract; and
    (D) evaporating solvent from the resulting purified solvent extract to obtain a yield of dried extract of about 25% by weight of the leaves employed in step (B).
2. The method of claim 1, wherein said solvent in step (B) is an alcohol having a purity of over 95%, and wherein step (B) is carried out at a temperature of lower than 20° C.
3. The method of claim 2, wherein said alcohol is methanol or ethanol.
4. The method of claim 1, wherein prior to step (C), step (B) is repeated three times over 18 hours, using 6 parts of said solvent per 1 part of said leaves .
5. The method of claim 1, wherein said purifying step (C) is carried out by:
    (i) evaporating the solvent at a reduced pressure to obtain a concentrated extract,
    (ii) dissolving the resulting concentrated extract in purified water to obtain a solution, and
    (iii) subjecting the resulting solution to sterile filtration to obtain a purified solvent extract.
6. The method of claim 1, wherein in step (D) the solvent is evaporated by freeze drying at a temperature of lower than 40° C., under a high vacuum, and heating at a temperature of lower than 35° C.
7. A method for reinforcing cellular immunity and delayed hypersensitivtty in a healthy human, comprising administering an effective amount of the *Olea europea* extract of claim 1 to a healthy human.

8. The method of claim 7, wherein the reinforcing of cellular immunity and delayed hypersensitivity is by activation and proliferation of T-lymphocytes, Natural Killer cells, monocytes and/or granulocytes, and the increase in pro-inflammatory cytokines.

9. The method of claim 8, wherein the activation and proliferation of T-lymphocytes, Natural Killer cells, monocytes and/or granulocytes is by an increase in cells with CD16, CD11b, CD11a, CD14, CD69 and/or CD25 expression.

10. The method of claim 7, wherein the reinforcing of cellular immunity and delayed hypersensitivity is by an increase in cytokines IL-1β and IL-8.

11. An *Olea europaea* extract having an oleuropein content of greater than 18% and a flavonoid content of greater than 5%, obtained by the method of claim 1.

* * * * *